United States Patent [19]

Schneider

[11] Patent Number: 5,267,967
[45] Date of Patent: Dec. 7, 1993

[54] RETENTION DEVICE

[75] Inventor: Barry L. Schneider, Buffalo Grove, Ill.

[73] Assignee: Hollister Incorporated, Libertyville, Ill.

[21] Appl. No.: 895,335

[22] Filed: Jun. 8, 1992

[51] Int. Cl.$^5$ .................... A61M 5/32; B65D 63/00; B65D 67/02
[52] U.S. Cl. ................ 604/174; 24/16 PB; 128/DIG. 6; 604/177; 604/178; 604/179; 604/180
[58] Field of Search .............. 128/DIG. 6, 604/174, 604/177-180; 24/16 PB, 17 AP, 30.5 P, 306; 248/74.2, 74.3

[56] References Cited

U.S. PATENT DOCUMENTS

| 2,979,794 | 4/1961 | Bartolo | 24/16 PB |
| 3,049,771 | 8/1962 | Litwin et al. | 24/16 |
| 3,542,321 | 11/1970 | Kahabka | 24/16 PB |
| 3,855,669 | 12/1974 | Meyer | 24/16 PB |
| 3,860,997 | 1/1975 | Van Riper, Jr. et al. | 24/16 PB |
| 3,900,023 | 8/1975 | Thomas | 24/16 PB |
| 3,908,233 | 9/1975 | Caveney | 24/16 PB |
| 3,991,444 | 11/1976 | Bailey | 24/16 PB |
| 4,236,280 | 12/1980 | Kreiseder | 24/16 PB |
| 4,272,047 | 6/1981 | Botka | 248/74 PB |
| 4,378,012 | 3/1983 | Brown | 128/207.17 |
| 4,392,857 | 7/1983 | Beran | 604/179 |
| 4,490,886 | 1/1985 | Omata | 24/16 PB |
| 4,665,588 | 5/1987 | Nakano | 24/16 PB |
| 4,699,616 | 10/1987 | Nowak et al. | 604/180 |
| 4,705,245 | 11/1987 | Osada | 248/74.3 |
| 4,805,856 | 2/1989 | Nicoli et al. | 248/74.3 |
| 4,874,380 | 10/1989 | Hesketh | 604/180 |
| 4,919,373 | 4/1990 | Caveny et al. | 248/74.3 |
| 5,073,170 | 12/1991 | Schneider | 604/180 |

FOREIGN PATENT DOCUMENTS 2142376 1/1985 United Kingdom ........... 248/74.2

Primary Examiner—Randall L. Green
Assistant Examiner—A. Zuttarelli
Attorney, Agent, or Firm—Tilton Fallon Lungmus

[57] ABSTRACT

A retention device, particularly useful for drainage tubes and the like, having a pad for adhesive attachment to a patient's skin at the exit/entry site for a post-surgical drainage tube. The device includes a retainer body secured to the pad and provided with a strap to be looped and tightened about the drainage tube for immobilizing that tube. A passage in the body receives the free end of the strap and a latching mechanism prevents retraction of the strap unless a pair of side flanges of the body are squeezed towards each other to alter the configuration of the body's top wall and cause upward disengagement of a restraining pawl from the ratchet teeth of the strap. In one form of the invention, the strap is oriented horizontally and the passage is spaced well above the pad so that the horizontal plane of the passage substantially bisects the loop along its axis, thereby allowing portions of the loop to be located above and below the entrance to the passage. In another embodiment, the strap is oriented in a vertical plane and the pawl is cammed laterally and upwardly to disengage the strap when the side flanges are squeezed towards each other.

25 Claims, 3 Drawing Sheets

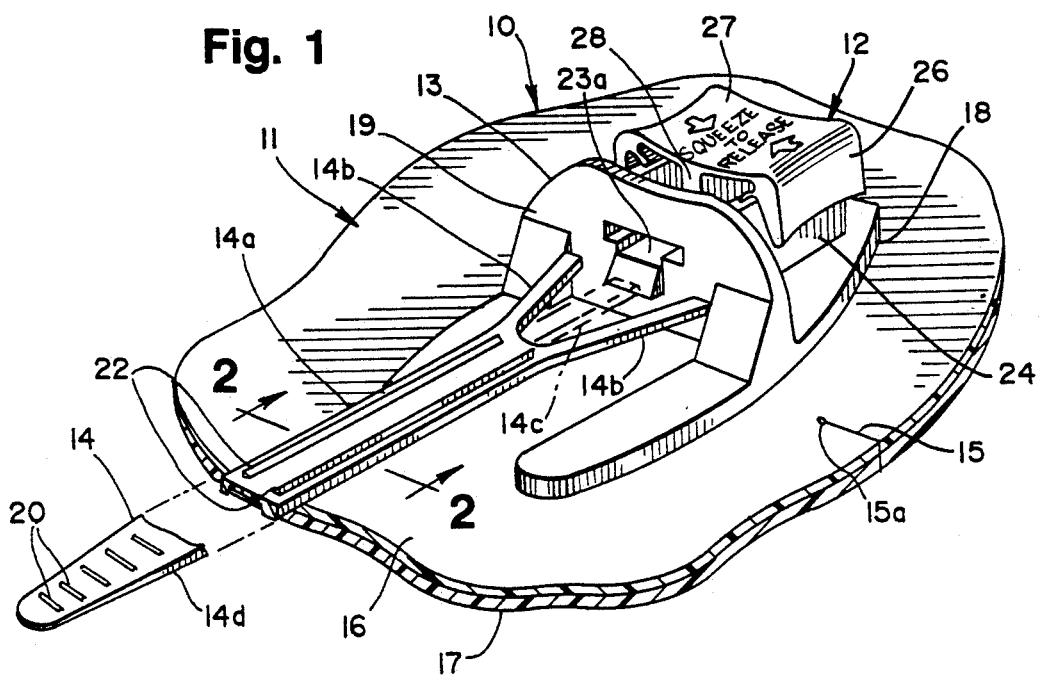
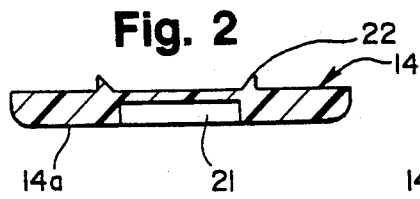
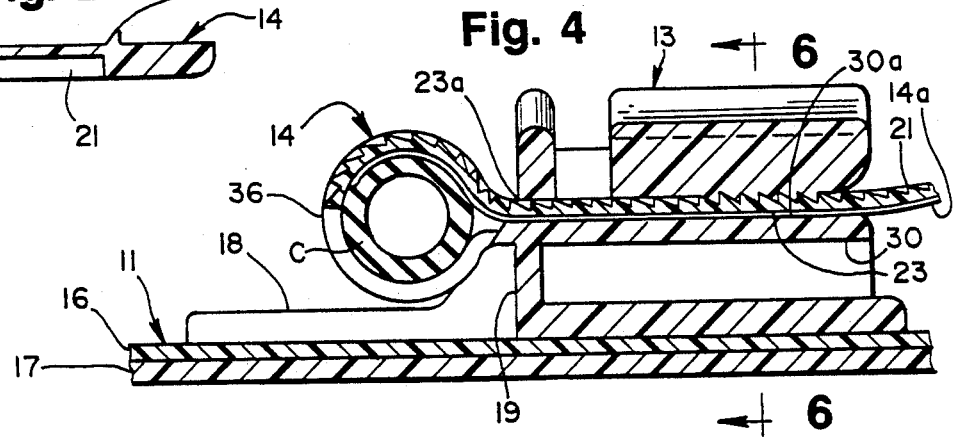
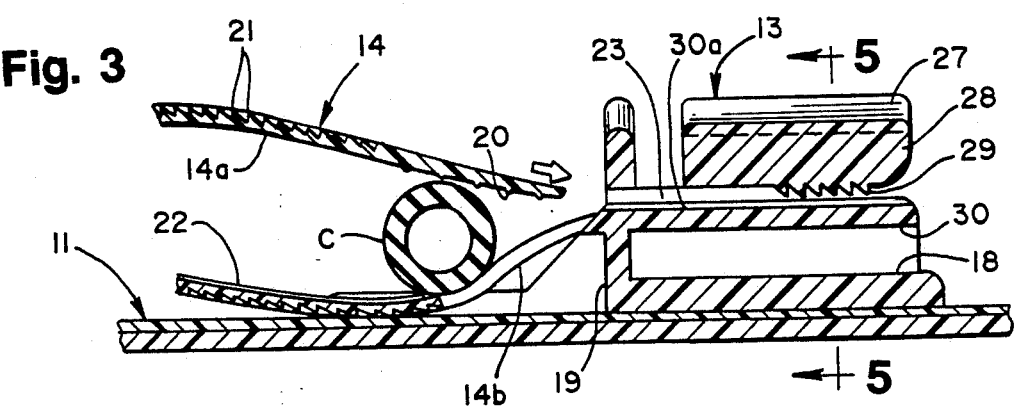

RETENTION DEVICE

BACKGROUND AND SUMMARY

Co-owned U.S. Pat. No. 5,073,170 discloses a retention device having an adhesive pad and a tube retainer secured to the pad's upper surface. A flexible strap extends from one side of the retainer and may be looped about a drainage tube so that when the strap's free end is inserted through a passage in the retainer body containing a detent or latch mechanism, the strap may be drawn tightly about the tube to immobilize the same. The Y-shaped configuration of the strap with its diverging arms secured to the retainer on opposite sides of the entrance opening to the passage permits the strap to be drawn tightly about even the smallest drainage tubes or catheters in common use.

While the patented device is highly effective in securing immobilizing drainage tubes over a wide range of sizes, the procedure for releasing the latching mechanism may not be immediately apparent to an attendant unfamiliar with the device. Such release involves lifting an exposed extension or handle of the latching member located within the passage. The lifting action may be awkward to perform and, even if done properly, may result in the transmission of pulling forces to the skin areas surrounding the exit site. Pulling or lifting forces applied to that site may cause considerable patient discomfort. To reduce such discomfort, the attendant may use the fingers of his/her other hand to restrain movement of the adhesive pad as the latching member is raised. While such a measure may avoid or reduce discomfort, it requires the use of both hands, leaving no hand free for the attendant to retract the strap from the passage when the latching member has been so raised.

In addition, it has now been found that while the patented device operates with a wide range of tube sizes and is especially effective in retaining drainage tubes of the smaller sizes (which prior retention devices often failed in securely restraining), the forces required to draw the strap tightly about larger-sized tubes tends to be greater than for smaller tubes because of the sharper directional change of the strap as it enters the retainer body. Again, the need for applying added force not only presents operational problems but would be expected to add to patient discomfort.

Accordingly, it is a main aspect of this invention to provide an improved tube retention device which is easily operated with tubes over the full range of sizes and which minimizes if not eliminates patient discomfort when the device is operated to secure or release a drainage tube. Problems of patient discomfort caused by the transmission of pushing or pulling forces towards or away from the skin surface are eliminated, or at least greatly reduced, because the forces required to operate the device are balanced and are not exerted in directions perpendicular to that surface. To release the latch mechanism, a user simply squeezes a pair of side flanges of the tube retainer with such opposing and offsetting forces being applied in directions parallel with the patient's skin.

Briefly, the device takes the form of a flexible pad having upper and lower surfaces and with a pressure-sensitive adhesive layer along its lower surface for adherence to a patient's skin. A tube retainer is mounted upon the pad's upper surface and includes a retainer body having a passage extending therethrough. An elongated strap has one end portion joined to the body adjacent the entrance to the passage and an opposite free end portion insertable into and through the passage. When so inserted, the strap forms a loop for receiving and holding a drainage tube.

In a preferred embodiment, the retainer body includes a pair of side walls extending along the passage, the side walls being pivotally connected along their upper edges to a pair of lever arms or side flanges. Such lever arms have relatively rigid lower portions extending downwardly below the upper edges of the side walls and spaced laterally from those side walls. The arms also have upper portions projecting above the edges, and a flexible top wall joins such upper portions. The top wall includes a central portion that normally curves downwardly into the passage but is forced into a partially straightened or raised condition when the rigid lower portions of the lever arms are pivoted towards each other. A pawl or latch member extends downwardly from the central portion of the top wall for engaging the ratchet teeth of the strap and preventing reverse movement of the strap in the passage unless and until the depending portions of the lever arms are squeezed towards each other between the operator's fingers.

The device may have its strap oriented so that the axis of the loop (or the plane of the strap) extends either horizontally or vertically. In an embodiment in which the orientation is horizontal, the strap is joined to the retainer body well above the plane of the pad, at approximately the level of the imperforate guide wall that defines the bottom surface of the passage through the retainer body. Ideally, that surface lies along a plane that substantially bisects the loop formed by the strap when the strap is tightened about a drainage tube. Approximately equal portions of the loop are thereby disposed above and below that plane to reduce the sharpness of curvature of the strap that would otherwise develop at the entrance to the passage if such portions were unequal in size.

A similar result occurs in an embodiment in which the strap is vertically oriented. In such a construction, however, the pawl has a laterally-directed and preferably angular latching surface and, in addition, the strap may have camming shoulder for directing the flexible latching member laterally out of engagement with the ratchet teeth of the strap when that member is raised by squeezing forces applied to the depending lever arms or flanges.

Other features, advantages, and objects of the invention will become apparent from the specification and drawings.

DRAWINGS

FIG. 1 is a fragmentary perspective view of a drainage tube attachment device embodying the invention.

FIG. 2 is an enlarged sectional view of the strap taken along line 2—2 of FIG. 1.

FIG. 3 is a fragmentary longitudinal sectional view showing the free end of the strap positioned for insertion into the passage of the retainer body.

FIG. 4 is a sectional view similar to (but on a scale slightly larger than) FIG. 3, showing the strap in latched condition drawn tightly about a drainage tube.

DETAILED DESCRIPTION OF PREFERRED EMBODIMENTS

Figure 5:
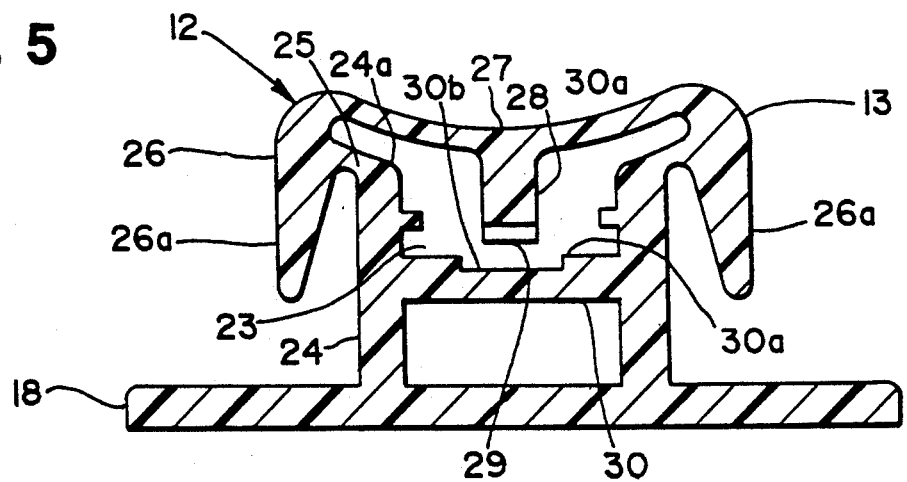
FIG. 5 is a still further enlarged cross sectional view taken along line 5—5 of FIG. 3.

Referring to FIGS. 1-7 of the drawings, numeral 10 generally designates a drainge tube retention device composed of a flexible adhesive pad 11 and retaining means 12 in the form of a retainer body 13 and an integral strap 14. The illustrated pad is planar and may have a periphery (not shown) of various shapes although circular is believed preferable. A radial entry slit 15 extends transversely with respect to the tube retainer, terminating in close proximity to that retainer. Preferably, the slit terminates with its inner end 15a near the center of the pad with the retainer 12 being offset from the pad's center point. Such a relationship, as disclosed in aforementioned U.S. Pat. No. 5,073,170, allows the pad to be centered over an exit opening for a drainage tube or catheter with the tube then extending generally upwardly through the center of the pad.

The materials and construction of the pad may be as disclosed in the aforementioned patent. In one such construction, pad 11 is composed of an upper layer 16 of resilient, flexible, fine-celled thermoplastic foam, such as polyolefin or polyurethane foam, and a lower layer 17 of soft, deformable skin barrier material having both wet and dry tack. If desired, the upper layer 16 may be formed of materials other than foam, such as a film of flexible polyurethane or other polymeric film having similar properties, and lower layer 17 may instead be formed of a suitable pressure-sensitive adhesive (e.g., a medical-grade acrylic adhesive).

The tube retainer 12 is a unitary part molded from polypropylene, nylon, or other flexible thermoplastic material and includes a generally planar plate 18 which is secured by adhesive or any other suitable means to the upper surface of pad 11. The retainer body 13 extends upwardly from the plate and includes a transverse front wall 19 to which one end of strap 14 is integrally joined. As in U.S. Pat. No. 5,073,170, strap 14 is Y-shaped in configuration and includes an elongated central tongue portion 14a and a pair of diverging limb portions 14b. The strap may also include a central limb portion 14c between the diverging portions 14b of the Y-shaped strap, although such central portion may be omitted if desired. The tongue portion of the strap is of substantially uniform width throughout its full length and the free end 14d is rounded and tapered. Free end 14d may also have a series of transverse ridges 20 to facilitate gripping the end of the strap between the fingers when the device is being readied for immobilizing a drainage tube. The underside of the tongue is provided with a longitudinal series of transversely extending ratchet teeth 21 and the upper surface may be provided with a pair of parallel, longitudinally-extending ribs 22.

The retainer body 13 has a horizontal passage 23 aligned with strap 14, the entrance 23a to the passage being located in the transverse front wall 19 between and slightly above the diverging arms or limbs 14b of the strap (FIGS. 1, 3). Referring to FIG. 5, the body 13 includes a pair of upstanding side walls 24 extending along passage 23 and pivotally connected at their upper ends by thin, flexible web portions 25 to a pair of lever arms or flanges 26. The lever arms 26 have relatively thick, rigid lower portions 26a extending downwardly below the webs (and below the upper edges 24a of the side walls) and upper portions 26b projecting above web portions 25. A flexible top wall 27 joins the upper portions of the two lever arms and, as shown clearly in FIG. 5, the top wall normally curves downwardly toward passage 23 when the body is in a relaxed or untensioned state (FIG. 5). In that state, the lever arms 26, and particularly the lower portions 26a of those arms, are spaced substantially from the outer surfaces of side walls 24.

Figure 6:
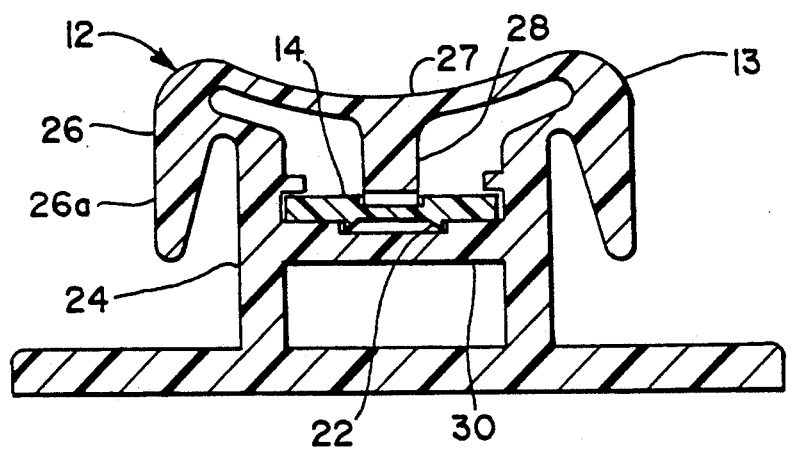
FIG. 6 is a cross sectional view similar to FIG. 5 but taken along line 6—6 of FIG. 4.
Figure 7:
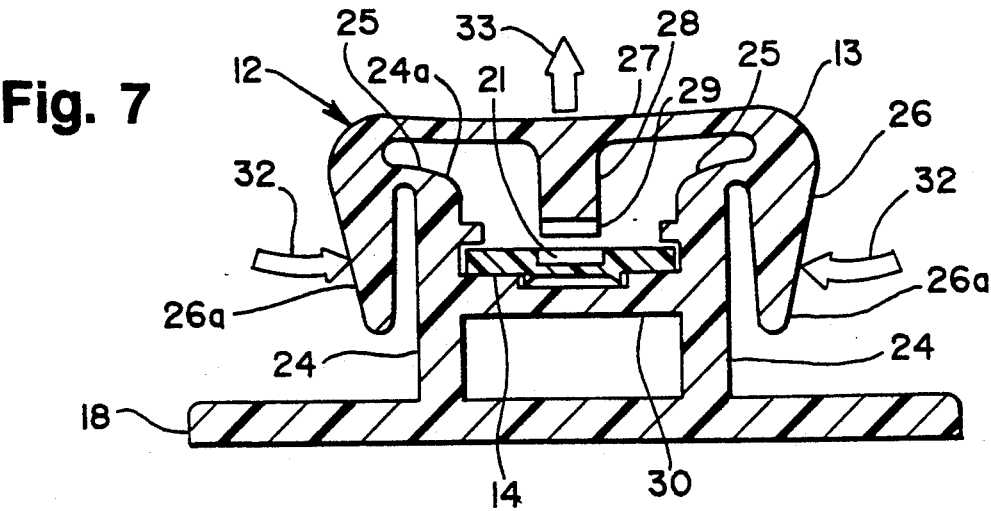
FIG. 7 is a cross sectional view similar to FIGS. 5 and 6 but showing the changes occurring when the lever arms of the retainer body are squeezed towards each other.

Detent means in the form of a latching member 28 is formed integrally with top wall 27 and projects downwardly from the central portion of that top wall. The latching member is provided with one or more teeth 29 (FIG. 3) and functions as a pawl for engaging the ratchet teeth of strap 14 when the strap is inserted into the passage as depicted in FIGS. 4 and 6.

Body 13 also includes a guide wall 30 which is parallel with plate 18 and pad 11 and has a top surface 30a spaced well above the upper surface of the pad. The guide wall is imperforate and includes an upwardly-facing channel 30b that extends the length of passage 23 and receives the longitudinal ribs 22 of the strap (FIG. 6).

The parts are dimensioned so that when the free end of the strap is inserted into passage 23 the ratchet teeth of the strap will engage the teeth of the pawl or latch member 28, causing top wall 27 to flex slightly upwardly as the teeth of the respective parts clear each other and then return a limited distance downwardly to maintain the teeth of the respective parts in forceful interlocking engagement. Retraction of the strap is prevented by the intermeshing teeth unless the top wall 27 and latch member 28 are lifted to shift the teeth of the pawl out of engagement with those of the strap.

Release of the latch mechanism occurs when the lever arms 26 along each side of the body 13 are squeezed towards each other in the directions of arrows 32 (FIG. 7), causing the arms to pivot about the webs 25 at the upper edges 24a of side walls 24 and producing at least a partial straightening of top wall 27. As the curvature in the top wall is reduced, the central portion of that wall shifts upwardly in the direction of arrow 33, lifting the teeth 29 of the latching member or pawl 28 out of engagement with teeth 21 of strap 14. Since the lower portions of the lever arms may be easily pivoted towards each other by the fingers of one hand, the user's other hand remains available to retract the strap from passage 23. The squeezing of the lever arms is facilitated by the fact that the outer surfaces of those arms are elongated in the direction of the passage and have concave curvatures revealed most clearly in FIG. 1. Since the lever arms 26 extend downwardly in the same directions as the user's fingers, the pivoting action of the lever arms corresponds with the closing action of the thumb and an opposing index or middle finger engaging the respective concave surfaces of the two arms.

Of particular importance is the fact that the forces exerted upon the retainer 12 to release the latching mechanism are applied in two opposing directions extending in a plane parallel with that of plate 18 and pad 11. As a result, release of the strap may be accomplished without pulling the device away from the wound site or pushing it towards that site. While lateral forces are applied to the device, those forces neutralize or balanced off against each other and, therefore, are not transmitted to any appreciable extent to the patient.

As shown in FIG. 4, when the device is in operative position strap 14 forms a loop 36 about a drainage tube or catheter C. Since the top surface 30a of guide wall 30 is spaced well above the upper surface of pad 11, the loop is free to center itself so that surface 30a is in a plane that substantially bisects the loop 36 and tube C along axial directions. Approximately equal portions of the loop are disposed above and below the plane of guide surface 30a. The change in direction of the strap loop as it enters passage 23 is generally matched by the change in direction of the strap at its point of origin where it commences its loop about tube C. The result is that the sharpness of the directional change of the strap adjacent passage entrance 23a is considerably less than would occur if the surface 30a of guide wall 30 were coplanar with the upper surface of pad 11. The disclosed construction permits tighter engagement of the strap about the tube for any given amount of tightening force applied to the strap and is particularly helpful in retaining larger-size tubes which require more abrupt changes in direction of the strap in the immediate vicinity of passage entrance 23a.

Figure 8:
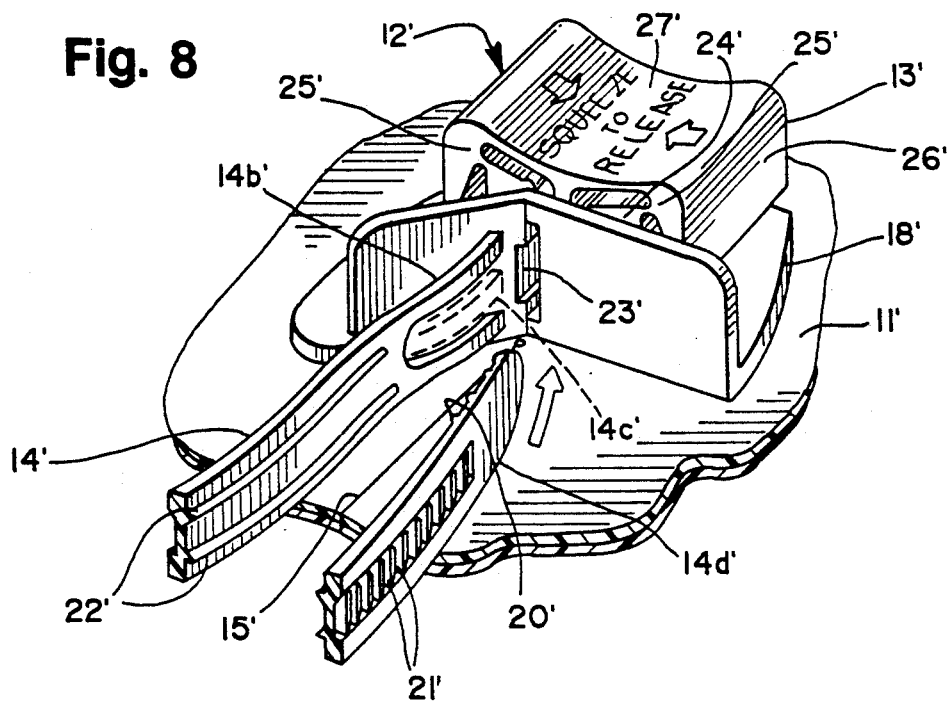
FIG. 8 is a fragmentary perspective view depicting a second embodiment of the invention in which the plane of the strap extends vertically.
Figure 9:
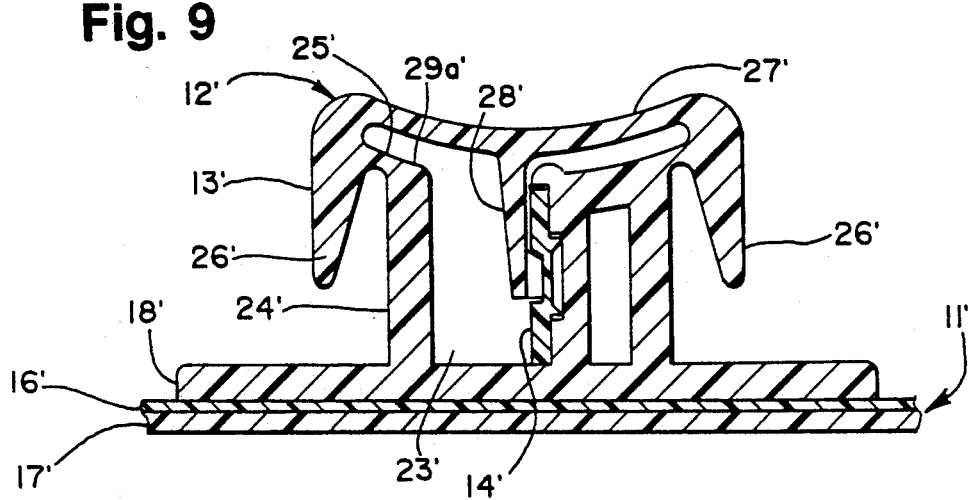
FIG. 9 is a cross sectional view illustrating the embodiment of FIG. 8 with the strap inserted and latched.
Figure 10:
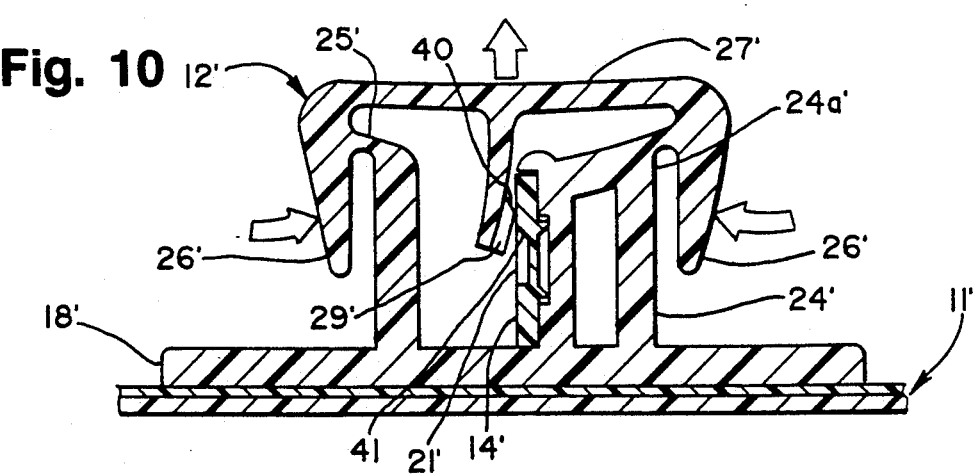
FIG. 10 is a sectional view similar to FIG. 9 but showing the lever arms squeezed towards each other for releasing the latch mechanism.

FIGS. 8-10 depict a second embodiment which is similar to the one already described except that the strap 14' of the tube retaining means 12' is oriented vertically rather than horizontally. The loop that is formed by the strap therefore has its axis extending vertically and wraps about the portion of a tube or catheter that exits the patient's body in a direction substantially perpendicular to the skin surface. Like retainer 12, retainer 12' includes a body 13' having side walls 24' that extend upwardly from a plate or base 18' secured to the upper surface of a pad 11'. Thin, flexible webs 25' connect the upper edge portions 24a' of the side walls 24' to relatively rigid lever arms or flanges 26'. When the lever arms are squeezed towards each other, they pivot about the connecting webs 25' to cause the flexible top wall 27' to straighten, at least partially, and its central portion to shift upwardly along with the latching member or pawl 28' that extend downwardly into passage 23'. Teeth 29' of the pawl face laterally to engage the teeth 21' of the strap when the parts are latched together. It will be observed from FIGS. 9 and 10 that the upper ends of latching teeth 29' slope to define camming surfaces 40 and the strap 14' may also have a mating sloping surface or shoulder 41. As a result, when lever arms 26' are pivoted inwardly to raise the latching member, the slope of surfaces 40 and/or 41 cams the flexible latching member laterally to release the strap for withdrawal from the passage.

In both of the embodiments of FIGS. 1-7 and 8-10, the squeezing forces for releasing the latch mechanisms are applied in opposing directions extending generally in planes parallel with plates 18 and 18'. While it is preferred that such squeezing forces cause the lever arms 26, 26' on both sides of the retainer bodies to pivot inwardly, thereby raising the central portions of top walls 27, 27', it should be understood that a similar lifting action might result if only one of the lever arms of each pair were capable of pivoting inwardly with the other arm of the same pair being stationary and simply serving as a brace against which the squeezing force would be applied. For example, referring to FIG. 9, if the tapered space between the left lever arm 26' and side wall 24' were instead occupied by the plastic material from which the remainder of the retainer is formed, the left arm would be non-pivotal but would nevertheless serve as a brace when squeezing forces are applied to both of the arms 26'. In such a case, the lifting action on pawl 28' would result solely from the inward pivotal movement of right arm 26' and the resulting changes in configuration of top wall 27'. Therefore, while it is preferred that both of the lever arms of the two embodiments be capable of pivotal movement, many of the advantages of the invention may be accomplished if only one of the arms is pivotally mounted. In either case, the squeezing force for releasing the latch mechanism will be applied in a direction parallel with plate member 18, 18'.

The retention devices embodying this invention are believed particularly useful in the medical area, especially where such devices include adhesive pads for attachment to a patient's skin in the vicinity of the entry or exit site of a catheter or other tube. However, the retainer body with its elongated strap, and the releasable latching mechanism provided by the body which releases when a squeezing force is applied to arms on opposite sides of the body, at least one of which is mounted for inward pivotal movement, may have other uses, some of which may be non-medical. Embodiments of the invention have therefore been disclosed in considerable detail for purposes of illustration, but it will be understood by those skilled in the art that many of these details may be varied without departing from the spirit and scope of the invention.

I claim:

1. A retention device for retaining elongate objects, comprising a retainer body having a passage extending therethrough and having an elongated strap with one end portion joined at a junction to said body and an opposite free end portion insertable into and through said passage to form said strap into an object-retaining loop; said strap having a longitudinal series of transversely-extending ratchet teeth along one surface thereof; said body including a pair of side walls having upper edges and extending along said passage; a pair of side arms joined to said side walls along opposite sides of said body; at least one of said arms being pivotally connected to one of said side walls along said upper edge thereof for pivotal movement towards and away from said one side wall; said arms also including upper portions projecting above said upper edges of said side walls; a flexible top wall joining said upper portions of said arms and having a central portion that is flexed into raised condition when said one arm is pivoted towards said one side wall; and latching means extending downwardly from said central portion of said top wall for engaging said teeth and preventing reverse movement of said strap in said passage; said latching means being lifted out of restraining engagement with said teeth when said arms are squeezed towards each other to cause pivotal movement of said one arm and upward flexure of said central portion of said top wall.

2. The device of claim 1 in which said passage has an entrance located adjacent the junction of said body and said one end of said strap.

3. The device of claim 1 in which both of said side arms are pivotally connected to said upper edges of said side walls for pivotal movement towards and away from said side walls.

4. The device of claims 1 or 3 in which said side arms include relatively rigid lower portions extending downwardly below said upper edges of said side walls.

5. The device of claim 4 in which said central portion of said top wall normally curves downwardly into said passage but is at least partially straightened when said latching means is lifted out of restraining engagement with said teeth of said strap.

6. The device of claim 1 in which said body is mounted upon a flexible pad having upper and lower surfaces and having a pressure-sensitive adhesive layer along its lower surface.

7. A drainage tube retention device comprising a flexible pad having upper and lower surfaces and having a pressure-sensitive adhesive layer along its lower surface for adherence of the pad to a patient's skin; and tube retaining means mounted upon said upper surface comprising a retainer body having a passage extending therethrough; an elongated strap having one end portion joined at a junction to said body and an opposite free end portion insertable into and through said passage to form said strap into a loop for receiving and holding a drainage tube; said strap having a longitudinal series of transversely-extending ratchet teeth along one surface thereof; said body having a pair of side walls extending along said passage; said side walls being pivotally connected along upper edges thereof to a pair of lever arms; said lever arms having relatively rigid lower portions extending downwardly below said edges and spaced laterally from said side walls and having upper portions projecting above said edges; and a flexible top wall joining said upper portions of said lever arms; said top wall having a central portion that normally curves downwardly into said passage when in an intensioned state but is raised and at least partially straightened when said lower portions of said lever arms are pivoted towards each other; and latching means extending downwardly from said central portion of said top wall for engaging said teeth and preventing reverse movement of said strap in said passage; said latching means being raised out of restraining engagement with said teeth when said lower portions of said lever arms are pivoted towards each other.

8. The device of claim 7 in which said passage has an entrance located adjacent the junction of said body and said one end of said strap.

9. The device of claim 7 in which said lever arms are elongated in a direction along said passage.

10. The device of claim 9 in which said lever arms have outer surfaces with concave longitudinal curvatures dimensioned for engaging and guiding a user's fingers when said lever arms are squeezed between the fingers and towards each other.

11. The device of claim 7 in which said body also includes a guide wall along said passage having an upper surface parallel with said pad.

12. The device of claim 11 in which said upper surface of said guide wall is spaced substantially above said pad.

13. The device of claims 11 or 12 in which said guide wall is imperforate.

14. The device of claims 11 or 12 in which said passage has a length and said guide wall includes an upwardly-facing channel extending the length of said passage.

15. The device of claim 14 in which said strap includes longitudinal rib means along the surface thereof opposite from said one surface; said rib means being slidably received in said channel.

16. The device of claim 12 in which said upper surface of said guide wall extends along a plane that substantially bisects said loop in an axial direction when said strap retains a drainage tube.

17. The device of claim 7 in which said body also includes a guide wall for said passage that is substantially perpendicular to said pad.

18. The device of claim 17 in which said guide wall is imperforate.

19. The device of claim 17 in which said guide wall includes a laterally-facing channel extending the length of said passage.

20. The device of claim 19 in which said strap includes longitudinal rib means along the surface thereof opposite from said one surface; said rib means being slidably receivable in said channel.

21. The device of claim 17 in which said guide wall extends along a plane that substantially bisects said loop in an axial direction when said strap retains a drainge tube.

22. The device of claim 11 in which said latching means includes a downwardly-facing pawl engagable with upwardly-facing ratchet teeth of said strap when said strap extends into said passage and is supported by said guide wall.

23. The device of claim 17 in which said latching means is provided with a lower end portion having a pawl that faces laterally towards said guide wall for engagement with said ratchet teeth when said strap extends into said passage and is supported by said guide wall; said latching means being laterally flexible; and camming means for directing said pawl out of engagement with said ratchet teeth when said latching means is raised.

24. The device of claim 23 in which said camming means includes a longitudinal shoulder provided by said strap alongside said ratchet teeth; said shoulder having a surface that slopes upwardly in a direction towards said top wall, when said strap is received in said passage, for camming said pawl laterally out of engagement with said ratchet teeth when said latching means is raised.

25. The device of claims 22 or 23 in which said camming means includes a sloping surface provided by said pawl for engaging said strap to cam said pawl laterally out of engagement with said ratchet teeth when said latching means is raised.

* * * * *